United States Patent
Lee et al.

(10) Patent No.: US 10,987,049 B2
(45) Date of Patent: Apr. 27, 2021

(54) SYSTEM AND METHOD FOR QUANTIFYING PIGMENTED LESION USING OCT

(71) Applicant: KOREA PHOTONICS TECHNOLOGY INSTITUTE, Gwangju (KR)

(72) Inventors: Byeong-il Lee, Gwangju (KR); In Hee Shin, Gwangju (KR); Joo Beom Eom, Gwangju (KR); Woosub Song, Gwangju (KR)

(73) Assignee: Korea Photonics Technology Institute, Gwangju (KR)

( * ) Notice: Subject to any disclaimer, the term of this patent is extended or adjusted under 35 U.S.C. 154(b) by 1166 days.

(21) Appl. No.: 14/883,666

(22) Filed: Oct. 15, 2015

(65) Prior Publication Data

US 2016/0235361 A1 Aug. 18, 2016

(30) Foreign Application Priority Data

Feb. 12, 2015 (KR) ........................ 10-2015-0021500

(51) Int. Cl.
 *A61B 5/00* (2006.01)
(52) U.S. Cl.
 CPC .......... *A61B 5/4848* (2013.01); *A61B 5/0066* (2013.01); *A61B 5/444* (2013.01); *A61B 5/445* (2013.01); *A61B 5/7257* (2013.01); *A61B 5/7278* (2013.01)
(58) Field of Classification Search
 CPC ............ G01B 9/02091; G01B 9/02044; A61B 5/0066; A61B 3/102; A61B 3/1225
 See application file for complete search history.

(56) References Cited

U.S. PATENT DOCUMENTS

| 7,586,957 B2 | 9/2009 | Sierra et al. |
| 7,929,579 B2 | 4/2011 | Hohm et al. |
| (Continued) | | |

FOREIGN PATENT DOCUMENTS

| JP | 2010-259698 A | 11/2010 |
| JP | 2013-108766 A | 6/2013 |
| (Continued) | | |

OTHER PUBLICATIONS

"Three-dimensional imaging of the human retina by high-speed optical coherence tomography" by C.K. Hitzenberger. Optics Express. vol. 11, No. 21, Oct. 2003, pp. 2753-2761 (Year: 2003).*

(Continued)

*Primary Examiner* — Jason M Ip

(74) *Attorney, Agent, or Firm* — Rabin & Berdo, P.C.

(57) ABSTRACT

Disclosed herein is a method for quantifying a pigmented lesion using Optical Coherence Tomography (OCT). The method includes (a) irradiating light and receiving an interference signal produced by reflection of the light from first and second boundary layers of a pigmented lesion; and (b) calculating size information of the pigmented lesion using phase information of the interference signal. According to embodiments of the present invention, there is an advantage of allowing calculation of size information of a pigmented lesion using OCT, by increasing a measurement range in the axial direction to which beams are irradiated.

5 Claims, 3 Drawing Sheets

(56) References Cited

U.S. PATENT DOCUMENTS

| | | | |
|---|---|---|---|
| 2010/0041986 A1* | 2/2010 | Nguyen | A61B 5/0066 600/427 |
| 2011/0028967 A1 | 2/2011 | Rollins et al. | |
| 2012/0086948 A1* | 4/2012 | Song | G01B 9/02028 356/479 |
| 2013/0235382 A1* | 9/2013 | Massow | A61B 3/102 356/479 |

FOREIGN PATENT DOCUMENTS

| | | |
|---|---|---|
| WO | WO 2007/035444 A2 | 3/2007 |
| WO | WO 2013/190991 A1 | 12/2013 |

OTHER PUBLICATIONS

"Quantitative differential phase measurement and imaging in transparent and turbid media by optical coherence tomography" by M. Sticker et al. Optics Letters. vol. 26, No. 8. Apr. 2001. pp. 518-520 (Year: 2001).*

* cited by examiner

SYSTEM AND METHOD FOR QUANTIFYING PIGMENTED LESION USING OCT

BACKGROUND OF THE INVENTION

1. Field of the Invention

The present invention relates generally to a system and method for quantifying a pigmented lesion using optical coherence tomography (OCT) and, more particularly, to a system and method for quantifying the extent of decomposition of a pigmented lesion, which is difficult to observe with the naked eye, to allow monitoring of skin treatments.

2. Description of the Related Art

As well known to those skilled in the art, there are various forms of pigmented lesions appearing on the skin, such as moles, freckles, blemishes, warts, blotches, OTA nevus, tattoos, etc. Pigmented legions generally develop when prolonged exposure to ultraviolet radiation causes the skin to produce excessive pigment melanin or aggregate nevus cells that produce the pigment melanin. Tattooing is the practice of creating wounds in the skin and intentionally inserting color pigments into the wounds.

In a medical context, tattoos may be defined as a condition in which color pigments are injected to the inside of the skin, which is the tough membrane on the inside of the skin. A photo laser may be selectively absorbed by particular pigment cells where a pigmented lesion exists. This absorption property of the photo laser has proven effective in surgery and cosmetic treatments during which minute rays of high-energy radiation induce localized heating and unwanted destruction of tissues. In this case, the duration and intensity of an optical pulse may influence the extent to which laser energy spreads to neighboring tissues and causes localized vaporization during the pulse.

A nanosecond pulsed laser, in the existing treatment process of pigmented lesions, may cause severe thermal damage to the skin due to its deep heat penetration. Thus, laser therapy controls the pulse length of a laser taking into account the size and position of the pigmented tissue, and irradiates optical energy only to the pigmented lesion according to selective photothermolysis. According to the photothermal effects, target nevus cells absorb laser energy to produce heat, which then spreads to neighboring tissues and induces thermal decomposition of the pigmented lesion.

However, since the common thermal relaxation time of the pigmented lesion is about 30 ns, which is shorter than the pulse length of a Q-switched laser, heat may penetrate into neighboring tissues. This may cause thermal damage and complications, making it difficult to remove perfectly a pigmented lesion. To overcome this problem, a pulse that is shorter than the thermal relaxation time of a pigmented lesion should be used to induce both photomechanical and photothermal effects. As for the theoretical stress relaxation time of the pigmented lesion, it falls within 30 to 200 picoseconds (ps), requiring very short time as compared to the nanosecond laser. Simultaneous photomechanical and photothermal effects corresponding to the stress relaxation time of the pigmented lesion may decompose the pigments into further smaller pieces by mechanical force while minimizing damage to the neighboring tissues.

As the pigmented lesion is decomposed into smaller pieces, macrophages in the body are easily removed or released through lymphatic vessels, i.e., the removal efficiency of the pigmented lesion becomes prominent. Recently, with advanced optical laser treatment technology, optical lasers are being developed by using a picosecond technology to transfer laser energy at a rate of up to a trillionth of a second. In this regard, U.S. Pat. Nos. 7,586,957 and 7,929,579 may be referenced.

However, there is no existing diagnostic system that can be coordinated with the laser treatment technology, making it impossible to monitor a change of the lesion under treatment in real time. General pigmented lesions under treatment have thus far been checked for a change in the outermost layer of the skin with the naked eye, to determine the development of the treatment. In order to verify the efficiency and reliability of removing the pigmented lesion, the pigmented lesion being removed needs to be quantitatively estimated. To optimize skin treatment monitoring and the treatment process, a technology is now required to measure an amount of decomposition of remaining pigment after a laser treatment and quantify the pigmented lesion.

In the meantime, Optical Coherence Tomography (OCT) uses the principle of interference of ripples to implement images of a living tissue. Specifically, OCT involves a light source to irradiate light to a tissue and a photo detector for detecting beams reflected from the tissue. The irradiated beam reflects off a layer of every depth inside the tissue, and the intensity of beams interfered on the photo detector is determined depending on a path difference between the reflected beams. OCT obtains information about a subject by measuring the intensity of the beams. Since beams used by OCT cannot typically penetrate deeply into the skin (deeper than around 2 mm), OCT has mainly been used in e.g., studies on the cell membrane or the retina. To obtain information about a pigmented lesion in the skin, it is beneficial to increase a measurement range in the axial direction in which rays are irradiated, and signals reflected and interfered from a tissue of a few to tens of nanometer (nm) size can be interpreted.

SUMMARY OF THE INVENTION

Accordingly, the present invention provides a system and method for quantifying a pigmented lesion using Optical Coherence Tomography (OCT) to determine an extent of decomposition of the pigmented lesion to which light for treatment is irradiated. The present invention also provides a system and method for estimating performance of a skin treatment, which is difficult to assess with the naked eye, with the help of the advanced laser treatment technology such as a picosecond laser.

The present invention also provides a system and method for calculating size information of a pigmented lesion using OCT by increasing a measurement range in the axial direction to which rays are irradiated.

In order to accomplish the above object, the present invention provides a method for quantifying a pigmented lesion using Optical Coherence Tomography (OCT). The method includes (a) irradiating light and receiving an interference signal produced by reflection of the light from first and second boundary layers of a pigmented lesion; and (b) calculating size information of the pigmented lesion using phase information of the interference signal.

Step (a) may include splitting the light into first and second split beams by a photo coupler; irradiating the first split beam to a reference stage able to adjust a path and the second split beam to a sample stage on which a subject having a pigmented lesion is placed; and receiving the interference signal produced by superposition of the first split beam reflected from the reference stage and the second split beam reflected from the first and second boundary layers of the pigmented lesion.

Step (a) may include controlling the reference stage such that a beam path difference of the first and second split beams is in a measurement range of a system.

Step (b) may include mapping a phase of the interference signal onto an image and calculating an amount of change of the phase from the image, and calculating size information of the pigmented lesion from the amount of change of the phase.

Step (b) may include Fourier-transforming the interference signal and mapping Fourier-transformed phase data onto a three dimensional (3D) image.

In order to accomplish the above object, the present invention also provides method for quantifying a pigmented lesion using Optical Coherence Tomography (OCT). The method includes (1) irradiating first light and receiving a first interference signal produced by reflection of the first light from first and second boundary layers of a pigmented lesion; (2) irradiating second light having a different wavelength from the first light and receiving a second interference signal produced by reflection of the second light from the first and second boundary layers; (3) calculating a mean wavelength from phase information of the first and second interference signals; and (4) calculating size information of the pigmented lesion using phase information of the first interference signal and the mean wavelength.

Step (1) may include splitting the first light into first and second split beams by a photo coupler; irradiating the first split beam to a reference stage able to adjust a path and the second split beam to a sample stage on which a subject having the pigmented lesion is placed; and receiving the first interference signal produced by superposition of the first split beam reflected from the reference stage and the second split beam reflected from the first and second boundary layers of the pigmented lesion.

Step (2) may include splitting the second light into third and fourth split beams by a photo coupler; irradiating the third split beam to a reference stage able to adjust a path and the fourth split beam to a sample stage on which a subject having the pigmented lesion is placed; and receiving the second interference signal produced by superposition of the third split beam reflected from the reference stage and the fourth split beam reflected from the first and second boundary layers of the pigmented lesion.

The method may further include controlling the reference stage such that an optical path difference of the first and second split beams is in a measurement range of a system.

Step (3) may include calculating the mean wavelength according to the following equation:

$$\Lambda = \frac{\lambda_1 \lambda_2}{|\lambda_2 - \lambda_1|}$$

where $\lambda$ is the mean wavelength, $\lambda_1$ is a wavelength of the first interference signal, and $\lambda_2$ is a wavelength of the second interference signal.

Step (4) may include Fourier-transforming the first interference signal to calculate phase data; and mapping the phase data and a value obtained by dividing the mean wavelength by two onto an image.

In order to accomplish the object, the present invention also provides a system for quantifying a pigmented lesion. The system includes a photo coupler for splitting light produced from a light source into first and second split beams; a reference stage, to which the first split beam is irradiated and which is able to adjust a path; a sample stage, to which the second split beam is irradiated and on which a subject having a pigmented lesion is placed; a photo detector for receiving an interference signal produced by superposition of the first split beam reflected from the reference stage and the second split beam reflected from first and second boundary layers of the pigmented lesion; and a controller for calculating size information of the pigmented lesion using phase information of the interference signal.

The controller may be configured to map a phase of the interference signal onto an image and calculate an amount of change of the phase from the image, and calculate size information of the pigmented lesion from the amount of change of the phase.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
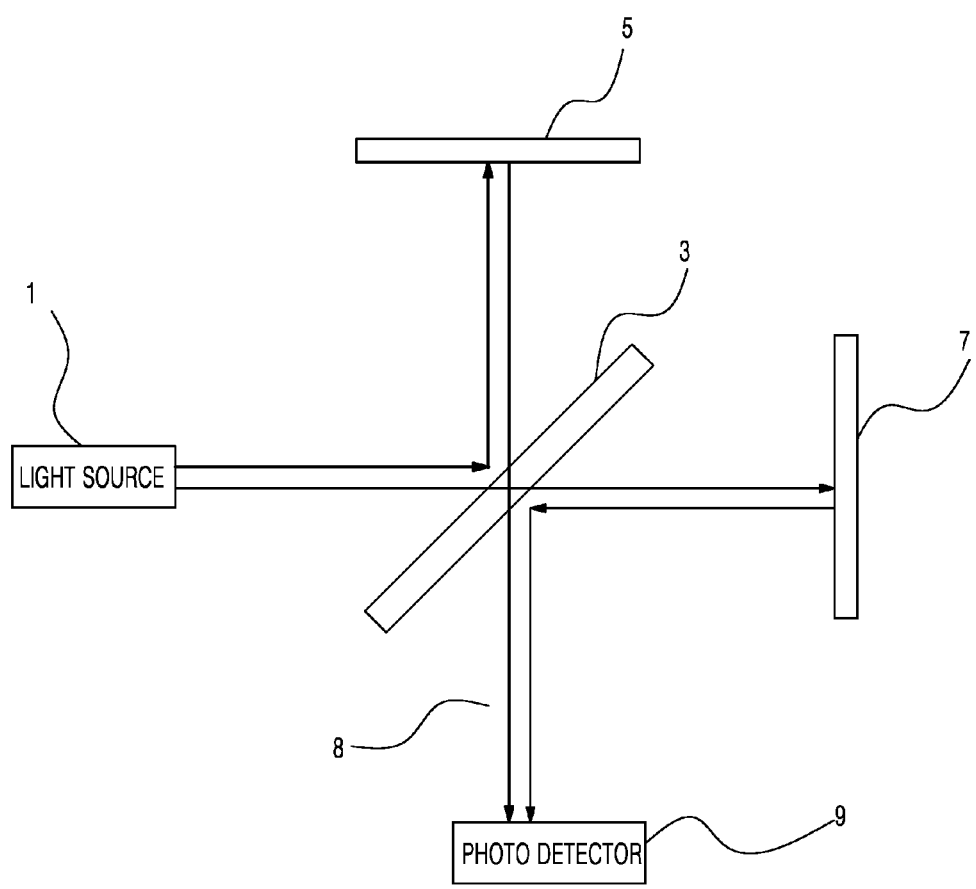
FIG. 1 shows a Michelson interferometer for explaining a concept of an interference signal.

The present invention will be described in detail below with reference to the accompanying drawings. Repeated descriptions and descriptions of known functions and configurations that have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

FIG. 1 shows a Michelson interferometer for explaining a concept of an interference signal. Referring to FIG. 1, a Michelson interferometer may include a light source 1, a beam splitter 3, a dynamic mirror 5, a fixed mirror 7, and a photo detector 9. Light emitted from the light source 1 is vertically split by the beam splitter 3. The split beams are incident on the dynamic mirror 5 and fixed mirror 7. The respective split beams reflected from the dynamic mirror 5 and fixed mirror 7 are recombined at the beam splitter 3 and incident on the photo detector 9 along a common path. Herein, the signal resulting from superposition of the beams each having thus far propagated along different paths is called an interference signal 8.

In general, to measure a size of an object, beams with a wavelength shorter than the size of the object may be used. However, when the interference signal 8 produced according to the light interference phenomenon is used, a size of an object may be measured even with the light with a wavelength longer than the object.

More specifically, measuring a size of an object may be seen as measuring a difference between distances to two boundary layers (hereinafter called a distance difference of two boundary layers) of the object. Since the boundary layers have different refractive indexes, part of the light is reflected while some is transmitted. Respective beams reflected from the two boundary layers reach the photo detector 9 with a time difference. Accordingly, the time difference of light contains distance information of the two boundary layers, which may be understood to have size information of the object as well. Using the time difference of beams reflected from the boundary layers may gain an advantage that measurement of an object as small as a few to tens of nanometers, such as cell tissues, does not require the use of light with a wavelength shorter than the size of the tissue.

However, the time difference between the reflected beams is typically a few to tens of picoseconds, making it difficult to measure the time difference. The interference signal 8 refers to a signal resulting from recombination of beams having traveled along different paths after being emitted from the light source 1. The beams appear as a single beam in the space according to the principle of superposition of light, and the interfered beams have different phases depending on difference between paths. Even if a distance between two boundary layers of a pigmented lesion is shorter than the wavelength of light, interfered beams represent phase changes, from which the distance difference may be measured.

The phase change of an interfered beam is expressed as in the following equation 1:

$$I \propto \cos\left(2\frac{2\pi}{\lambda}\Delta L\right) \quad (1)$$

where I represents an intensity of the light, λ represents a wavelength of the light, and λL represents a distance difference of two boundary layers. Existing OCT technology calculates information about the pigmented lesion with the intensity of light detected according to the aforementioned principle. However, the intensity of the interference signal of light given by the same distance difference is not an absolute value and may vary because it is affected by reflectivity and transmittance of the boundary layer and absorptivity of the object. Accordingly, measurements of the size of the pigmented lesion using only the intensity of the interference signal may be inaccurate.

In the following embodiments, provided is a system and method for quantifying a size of a pigmented lesion by controlling the interference signal and phase-shifting the controlled signal.

Figure 2:
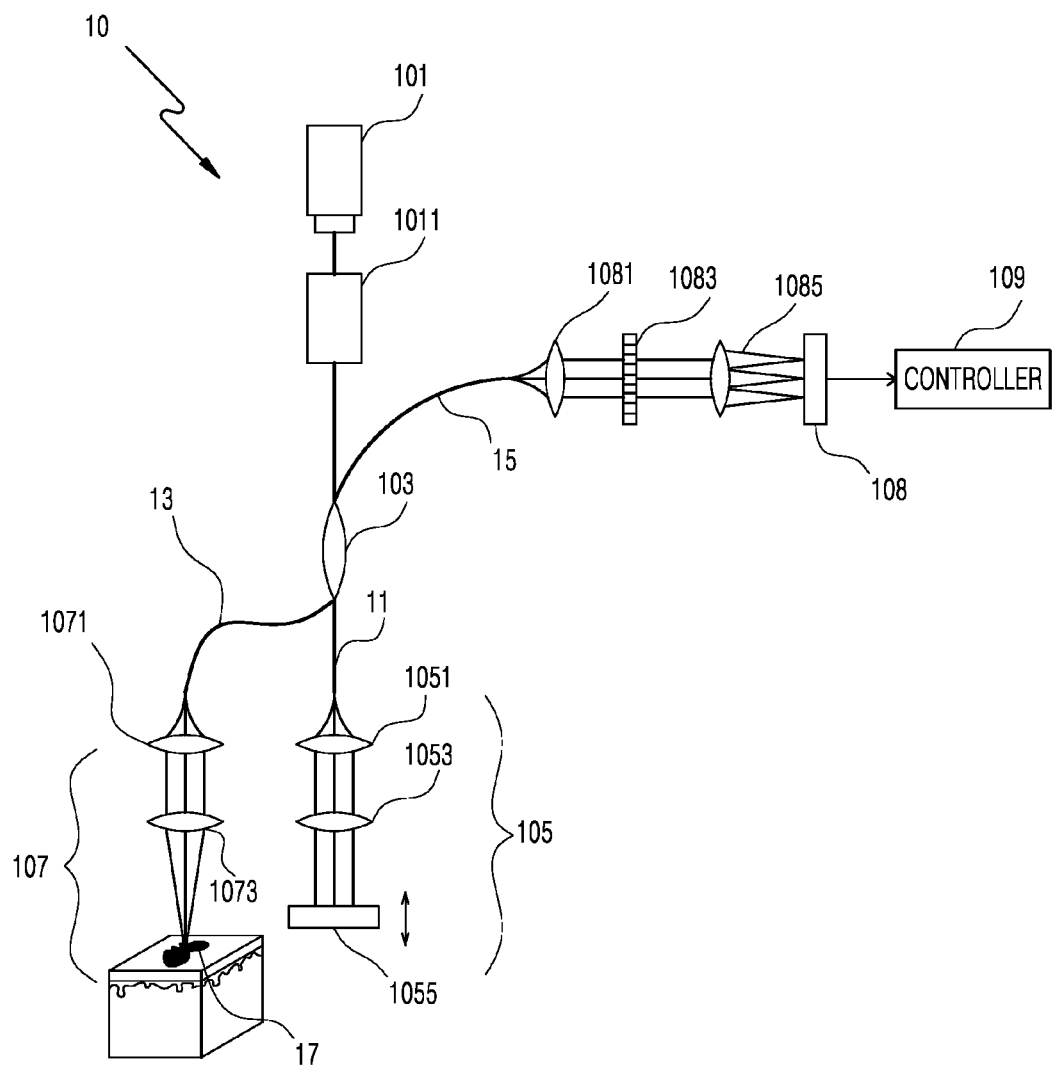
FIG. 2 is a diagram of a system for quantifying a pigmented lesion using Optical Coherence Tomography (OCT), according to an embodiment of the present invention.

FIG. 2 is a diagram of a system for quantifying a pigmented lesion using OCT, according to an embodiment of the present invention. Referring to FIG. 2, a system 10 for quantifying a pigmented lesion may include a light source 101, a photo coupler 103, a reference stage 105, a sample stage 107, a photo detector 108, and a controller 109. In the embodiment, for an interferometer for interference, a Mach-Zehnder interferometer may be used. In addition, a common path interferometer may be used in which the reference stage 105 and the sample stage 107 are integrated into one unit.

The light source 101 may emit light for diagnosis to provide monitoring information for diagnosis for a human skin 17. In the embodiment of the present invention, the light for diagnosis emitted from the light source 101 may be used to quantify a size of a pigmented lesion on the skin 17. There may be an isolator 1011 installed on the path of the light for diagnosis. The isolator 1011 may block the light for diagnosis emitted from the light source 101 from returning back to the light source 101.

The light for diagnosis emitted from the light source 101 is incident on the photo coupler 103. The photo coupler 103 may split and output the incident light for diagnosis toward the reference stage 105 and the sample stage 107. Furthermore, the photo coupler 103 may output an interference signal 15 produced by reflection from the reference stage 105 and the sample stage 107 toward the photo detector 108.

The reference stage 105 may include a reference mirror 1055, a focusing lens 1053, and a collimating lens 1051. The reference mirror 1055 may be arranged to reflect a first split beam 11 split by the photo coupler 103 to be incident back on the photo coupler 103. The reference mirror 1055 is capable of linear reciprocating motion in order to control a path length of the first split beam 11. The reference mirror 1055 may set the path length of the incident first split beam 11 beforehand, or control the path length of the first split beam 11 as necessary.

The collimating lens 1051 may be arranged between the reference mirror 1055 and the photo coupler 103 for collimating the spread first split beam 11. The focusing lens 1053 may be arranged between the collimating lens 1051 and the reference mirror 1055 for focusing the first split beam 11 onto the reference mirror 1055.

The sample stage 107 may be comprised of a collimating lens 1071 and a focusing lens 1073, and a subject 17 with a pigmented lesion may be fixedly placed on the sample stage 107.

The light for diagnosis may be irradiated onto the pigmented lesion 17 following irradiation of light for treatment or simultaneously with irradiation of the light for treatment. A second split beam 13 irradiated onto the pigmented legion 17 may reflect off the boundary layer of the pigmented lesion 17. The sample stage 107 may two-dimensionally scan the reflected second split beam 13 to obtain three dimensional (3D) phase information of the interference signal 15. An MEMS mirror may be used for the two dimensional (2D) scanner.

The reflected second split beam 13 may include a first reflected beam reflected from the first boundary layer of the pigmented lesion 17 and a second reflected beam reflected from the second boundary layer of the pigmented lesion 17.

The second reflected beam of the second split beam 13 is incident back onto the photo coupler 103 with a slight time difference from the first reflected beam. As a result, the photo coupler 103 may output the reference signal 15 resulting from superposition of the first split beam 11, which is incident back onto the photo coupler 103, and the first and second reflected beams.

The collimating lens 1071 may be arranged between the pigmented lesion 17 and the photo coupler 103 for collimating the spread second split beam 13. Furthermore, the focusing lens 1073 may be arranged between the collimating lens 1071 and the pigmented lesion 17 for focusing the second split beam 13 onto the pigmented lesion 17.

The photo detector 108 may receive the interference signal 15 produced by superposition of the first split beam 11 incident back onto the photo coupler 103, and the second split beam 13. The photo detector 108 may be comprised of photo diodes if the light produced from the light source 101 is from a variable wavelength light source, or may include a spectroscope using a diffraction grating 1083.

In the embodiment of the present invention, with an interferometer comprised of the reference stage 105 and the sample stage 107, unlike intensity of a beam being determined only by a difference in distance between boundary layers of the pigmented lesion 17, the interference signal 15 is produced by differences of paths to the respective boundary layers on which beams are reflected from the reference stage 105 and the sample sage 107.

Assuming that the distance difference between the two boundary layers of the pigmented lesion 17 is d, a corresponding interference signal of the first and second reflected beams is produced, which may be seen as the second split beam 13. In addition, assuming that a beam path distance of the reference stage is $L_1$ and a beam path distance to the first boundary layer of the pigmented lesion 17 is $L_2$, a beam path distance to the second boundary layer of the pigmented lesion 17 is $L_2+d$. In this case, a first path difference of $L_1-L_2$ and a second path difference of $L_1-(L_2+d)$ exist for the reference signal 15. More specifically, the first path difference is a path difference between first reflected beams of the first and second split beams 11 and 13 reflected from the first boundary layer, and the second path difference is a path distance of second reflected beams of the first and second split beams 11 and 13 reflected from the second boundary layer. An interference fringe corresponding to each path difference has an intensity of light determined by the equation 1. In the embodiment of the present invention, as a path of the reference mirror 1055 varies, the path difference change, which changes both the first and second path differences. That is, for the reference signal 15, the two path differences are determined according to a function of the path length of the reference mirror 1055, and controlling the path difference ΔL means that a phase value $$\cos\left(2\frac{2\pi}{\lambda}\Delta L\right)$$

of the reference signal 15 may be controlled according to the equation 1.

Examining the phase value $$\cos\left(2\frac{2\pi}{\lambda}\Delta L\right)$$

of the reference signal 15, if the path difference ΔL is 0, the cosine function has the maximum value and the brightest interference signal 15 is measured at the photo detector 18. If there is no interferometer, information of path difference ΔL=0 is not meaningful because it is almost like there is no size information. On the other hand, in the embodiment of the present invention where an interferometer exists, a phase value of the interference signal 15 according to the path difference is meaningful. In a case that there is an interferometer of the reference stage 105 and sample stage 107, the brightest reference signal 15 is measured when a beam path length of the reference mirror 1055 is $L_2$ or $L_2+d$, making the phase of the interference signal 15 become 0. However, the system has limitations on a measurement range of the beam path difference.

The user may control the reference mirror 1055 such that the beam path difference of the first and second split beams 11 and 13 is within a measurement range of the system. The path difference of the reference stage 105 and sample stage 107 may be expressed as $L_{offset}=L_1-L_2$. In an ordinary system, the range of measurable path differences is restricted. The $L_{offset}$ measurement range of the system is generally within a few millimeters. Accordingly, the user needs to control the reference mirror 1055 such that the value of $L_{offset}$ may be in a measurable range. Afterwards, the user may fix the reference mirror 1055 to measure the reference signal 15.

A path difference for respective boundary layers of the sample stage 107 represents size information of the pigmented lesion 17. The path difference is too small to be measured as a distance variable. An existing OCT obtains a tomogram of a skin by calculating a path difference for boundary layers of a subject from the length of an intensity wave of interfered light that changes peak to peak. However, with the existing OCT that uses a change of light intensity, it is not possible to measure the size of a tissue of the pigmented lesion 17, which is shorter than the wavelength of light. This is because thickness of an object cannot be identified if a coherent distance that the light source 1 has is wider than the thickness of the object.

Accordingly, in the embodiment of the present disclosure, not the beam intensity but the phase information of the beam is used to calculate the path difference for boundary layers of a subject. Using the phase information of the reference signal 15 has an advantage of obtaining information about a path difference below the light source wavelength. This will be described later in connection with FIG. 3.

If beams produced from the light source 101 are wideband beams, the collimating lens 1081, the diffraction grating 1083, and the focusing lens 1085 may be arranged between the photo detector 108 and the photo coupler 103. The collimating lens 1081 collimates the spread interference signal 15. The diffraction grating 1083 may separate beams of the interference signal 15 by wavelength. The focusing lens 1085 focuses the interference signal 15 that went through the diffraction grating 1083 on the photo detector 108.

The controller 109 may analyze the phase of the interference signal 15 received by the photo detector 108 to calculate size information of the pigmented lesion. Although not shown, the controller 109 may include a display for visualizing and displaying the size information of the pigmented lesion in graph(s).

A method for quantifying a pigmented lesion in accordance with an embodiment of the present invention will now be described.

In an embodiment, a method for quantifying a pigmented lesion includes (a) irradiating light from the light source 101 and receiving the interference signal 15 produced by reflection of the light from first and second boundary layers of the pigmented lesion 17; and (b) calculating size information of the pigmented lesion 17 using phase information of the interference signal 15.

Step (a) may include splitting the light emitted from the light source 101 into the first split beam 11 and the second split beam 13, by the photo coupler 103; irradiating the first split beam 11 to the reference stage 105 that may adjust a path, and irradiating the second split beam 13 to the sample stage 107 on which a subject having the pigmented lesion 17 is placed; and receiving the interference signal 15 produced by superposition of the first split beam 11 reflected from the reference stage 105 and the second split beam 13 reflected from the first and second boundary layers of the pigmented lesion 17. The reflected second split beam 13 is a term that includes, as described above, the first reflected beam reflected from the first boundary layer of the pigmented lesion 17 and the second reflected beam reflected from the second boundary layer.

Furthermore, step (a) may further include controlling the reference stage 105 such that a beam path difference of the first and second split beams 11 and 13 is within a measurement range of the system. In this case, the value $L_{offset}$ is adjusted by changing a path length of the first split beam 11 by controlling the reference mirror 1055 of the reference stage 105.

Step (b) may be performed by the controller 109. Step (b) may include extracting phase data of the reference signal 15. Step (b) may include mapping the extracted phase data onto a 2D image, calculating an amount of phase change from the image, and calculating size information of the pigmented lesion 17 from the amount of phase change. In this case, step (b) may includes Fourier-transforming the interference signal 15 and mapping the Fourier-transformed phase data onto the 2D image.

The interference signal 15 detected by the photo detector 108 includes intensity and phase information of the light as expressed in the equation 1. A result of the Fourier transform in step (b) is expressed in the following equation 2:

$$FFT(I) \propto E(2nL)\exp(\pm j2nk\Delta L) \qquad (2)$$

where FFT(I) represents the Fourier-transformed reference signal 15, E(2nL) represents a system constant, and $2nk\Delta L$ in the exponential term represents phase information of the reference signal 15. Step (b) may include measuring the phase $\Phi = 2nk\Delta L$ of the reference signal 15 over time. Step (b) may implement a phase image from the measured phase data. The individual phase data may be three-dimensionally phase-mapped by 2D scanning.

Figure 4:
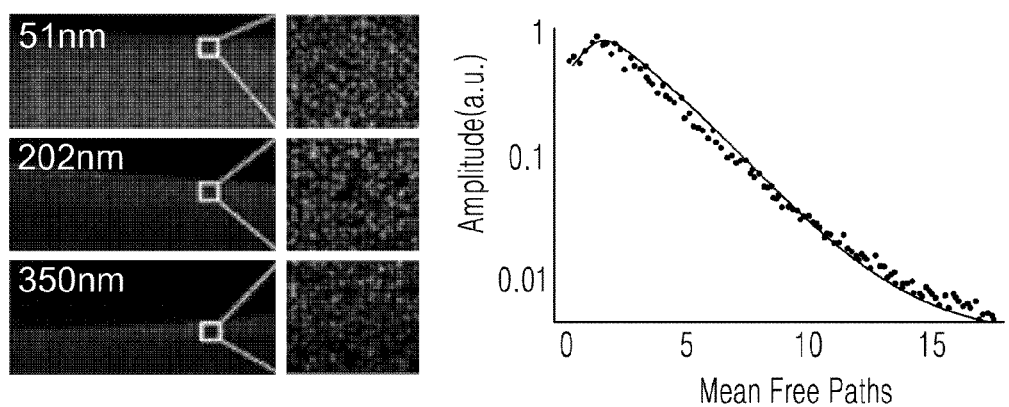
FIG. 4 shows graphs resulting from measurement of amounts of phase changes due to changes of a mean free path in an image onto which phase data is mapped.

Step (b) may include calculating an amount of phase change by computing a change in mean free path according to scattering characteristics per particle size from the three dimensionally phase-mapped image. Since $k=2\pi/\lambda$, phase difference $\Delta L$ may be calculated and represented as $$\Delta L = \frac{\lambda}{4\pi n}\Delta\Phi$$

by measurement of the phase value. FIG. 4 shows graphs resulting from measurement of amounts of phase changes due to changes of a mean free path in an image onto which phase data is mapped.

Step (b) may include dividing the amount of phase change at certain unit intervals to visualize the measurement result in a histogram. In this case, the phase information in measurement space is combined information in the optical axis on the 3D subject, and information per size of the pigmented lesion 17 may be calculated in ratios. For example, ratios of 10% for 1um or less, 5% for 1 to 10 um, 10% for 10 to 60 um, 20% for 50 to 100 um, 20% for 100 to 200 um, and 10% for 200 to 400 um may be represented in a graph.

A maximum measurement range of the path difference in consideration of light coherence distance corresponds to a value obtained by dividing a wavelength of the irradiated light in half. As the phase $\Phi$ of the interference signal 15 varies within a range of 0 to $2\pi$ radians, the maximum measurement range in the direction of optical axis of the irradiated light (measurement range of path difference) becomes $\lambda/2n$.

In another embodiment of a method for quantifying a pigmented lesion, to obtain information about pigmented lesions in the subcutaneous layer, it is desirable to increase the measurement range in the direction of optical axis. The measurement range may be increased by combining phases of two signals with different wavelengths to calculate a new mean wavelength. The newly calculated mean wavelength may be longer than that of the existing beam, thereby expanding the measurement range of the photo detector.

Figure 3:
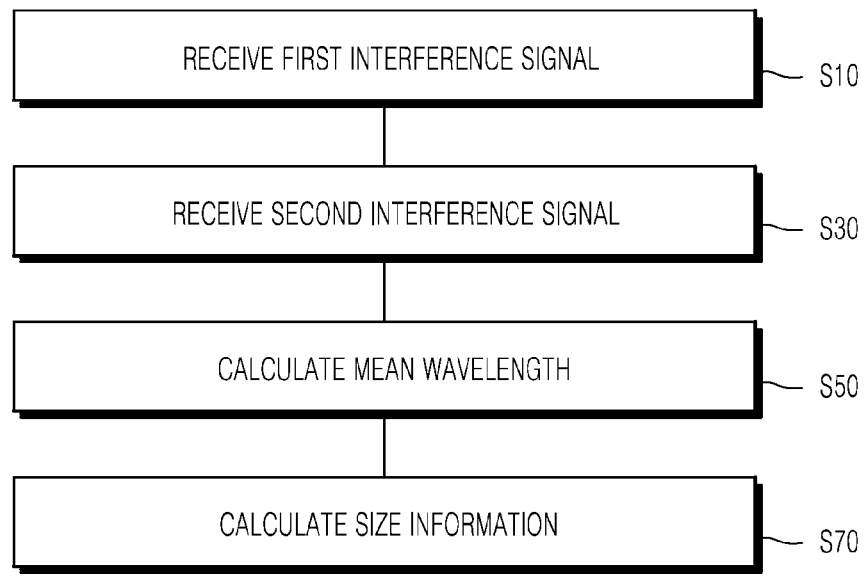
FIG. 3 is a flowchart illustrating a method for quantifying a pigmented lesion using OCT, according to an embodiment of the present invention.

FIG. 3 is a flowchart illustrating a method for quantifying a pigmented lesion using OCT, according to an embodiment of the present invention. Referring to FIG. 3, a method for quantifying a pigmented lesion using the OCT may include receiving a first reference signal in step S10, receiving a second reference signal in step S30, calculating a mean wavelength in step S50, and calculating size information of a pigmented lesion in step S70.

Receiving a first reference signal in step S10 includes irradiating a first beam from the light source 101 and receiving a first reference signal 15a produced by reflection of the first beam from first and second boundary layers of the pigmented lesion 17.

Receiving a second reference signal in step S30 includes irradiating a second beam with a wavelength different from that of the first beam from the light source 101 and receiving a second reference signal 15b produced by reflection of the second beam from the first and second boundary layers.

Calculating a mean wavelength in step S50 may include calculating a new mean wavelength using phase information of the first and second interference signals 15a and 15b. Calculating size information of a pigmented lesion in step 70 may include calculating size information of a pigmented lesion using phase information of the first interference signal 15a or the second interference signal 15b and the calculated mean wavelength.

Receiving a first interference signal in step S10 may include splitting the first beam into a first split beam 11a and a second split beam 13a by the photo coupler 103; irradiating the first split beam 11a to the reference stage 105 that may adjust a path and irradiating the second split beam 13a to the sample stage 107 on which a subject having the pigmented lesion 17 is placed; and receiving the first interference signal 15a produced by superposition of the first split beam 11a reflected from the reference stage 105 and the second split beam 13a reflected from the first and second boundary layers of the pigmented lesion 17. In this case, the user may control the reference mirror 1055 such that the beam path difference of the first and second split beams 11a and 13a is within a measurement range of the system.

Receiving a second interference signal in step S30 may include splitting the second beam into a third split beam 11b and a fourth split beam 13b by the photo coupler 103; irradiating the third split beam 11b to the reference stage 105 that may adjust a path and irradiating the fourth split beam 13b to the sample stage 107 on which the subject having the pigmented lesion 17 is placed; and receiving the second interference signal 15b produced by superposition of the third split beam 11b reflected from the reference stage 105 and the fourth split beam 13b reflected from the first and second boundary layers of the pigmented lesion 17.

Calculating a mean wavelength in step S50 may be performed by the controller 109. Calculating a mean wavelength in step S50 may include calculating a new mean wavelength according to the following equation 3:

$$\Lambda = \frac{\lambda_1 \lambda_2}{|\lambda_2 - \lambda_1|} \qquad (3)$$

where $\lambda$ refers to a calculated mean wavelength, $\lambda_1$ refers to a wavelength of the first interference signal 15a, and $\lambda_2$ refers to a wavelength of the second interference signal 15b. The mean wavelength $\lambda$ may be calculated by the user beforehand by measuring the first and second beams before the light is irradiated to a subject for measurement. The user may calculate and use a mean wavelength λ to suit the depth of the pigmented lesion 17 that exists in the subject.

Calculating size information in step S70 may be performed by the controller 109. The method may further include calculating phase data by Fourier-transforming the first interference signal 15a; and mapping the phase data and a value obtained by dividing the calculated mean wavelength λ by 2 onto a 3D image. Calculating phase data by Fourier-transforming the first interference signal 15a is performed as in step (b).

All beam phase measuring devices including the existing OCT have a problem of phase wrapping (2π ambiguity). It means that if the beam phase measuring device measures a phase in a range of 0 to 2π and converts it into a unit corresponding to a change of the sample and the change of the sample exceeds 2π, phase jumps occur, which causes confusion in the measurement results. Considering this, calculating size information in step S70 obtains a final phase image by adding a value obtained by dividing the calculated mean wavelength λ by 2 to the phase data during a phase imaging process. The value obtained by dividing the mean wavelength λ by 2 represents how many times phase jumping occurs.

Effects of phase wrapping and increases in the measurement range by calculating a mean wavelength in step S50 and calculating size information in step S70 are disclosed in Korean Patent No. 10-1308433 issued to the co-applicant, so the details will be omitted herein.

The embodiments of the present disclosure gains advantages of improving measurement accuracy by controlling the phase of an interference signal with an interferometer, and quantifying information about an object having a smaller size than a wavelength of an irradiated beam by extracting not intensity but phase information of the beam.

As described above, according to embodiments of the present invention, there is an advantage of allowing calculation of size information of a pigmented lesion using OCT, by increasing a measurement range in the axial direction to which beams are irradiated.

According to embodiments of the present invention, there is another advantage of allowing monitoring of development of a treatment by visualizing an extent of decomposition of a pigmented lesion using an amount of phase change of an interference signal. Furthermore, with advanced laser treatment technology such as a picosecond laser, embodiments of the present invention provide another advantage of allowing estimation of skin treatment performance of a laser treatment device, which is difficult to assess with the naked eye.

Moreover, embodiments of the present invention provide another advantage of allowing verification of efficiency and reliability in removal of a pigmented lesion by determining a quantitative extent of decomposition of the pigmented lesion.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for quantifying a pigmented lesion using Optical Coherence Tomography (OCT), the method comprising:
    (a) irradiating light and receiving an interference signal produced by reflection of the light from first and second boundary layers of a pigmented lesion; and
    (b) calculating size information of the pigmented lesion using phase information of the interference signal;
  wherein step (a) comprises:
    splitting the light into first and second split beams by a photo coupler; and
    irradiating the first split beam to a reference stage including a reference mirror configured to adjust a path, and irradiating the second split beam to a sample stage on which a subject having the pigmented lesion is placed;
    the interference signal being produced by superposition of the first split beam reflected from the reference stage and the second split beam reflected from the first and second boundary layers of the pigmented lesion, the reflected second split beam including a first boundary layer reflected split beam and a second boundary layer reflected split beam;
    a beam path distance corresponding to the first split beam being $L_1$, a beam path distance corresponding to the first boundary layer reflected split beam being $L_2$, and a beam path distance corresponding to the second boundary layer reflected split beam being $L_2+d$, d being a distance difference between the first boundary layer and the second boundary layer; and
    a first path difference being $L_1-L_2$ and a second path difference being $L_1-(L_2+d)$;
  wherein
    the interference signal corresponds to the first path difference and the second path difference;
    step (a) further comprises controlling the reference mirror to adjust $L_{offset}$, wherein $L_{offset}=L_1-L_2$, by changing a path length of the first split beam so that $L_{offset}$ is within a predetermined range; wherein the sample stage is configured to two-dimensionally scan the second split beam to obtain three dimensional (3D) phase information of a phase of the interference signal; and
    wherein step (b) comprises calculating an amount of change in the phase by computing a change in mean free path according to scattering characteristics per particle size from a three dimensionally phase-mapped image corresponding to phase data measured for the interference signal.

2. The method of claim 1, wherein step (b) further comprises:
    mapping the phase of the interference signal onto an image and calculating the amount of change of the phase from the image, and
    calculating size information of the pigmented lesion from the amount of change of the phase.

3. The method of claim 2, wherein step (b) comprises:
    Fourier-transforming the interference signal and mapping Fourier-transformed phase data onto a three dimensional (3D) image.

4. A system for quantifying a pigmented lesion, the system comprising:
    a photo coupler for splitting light produced from a light source into first and second split beams;
    a reference stage including a reference mirror, to which the first split beam is irradiated and which is configured to adjust a path;
    a sample stage, to which the second split beam is irradiated and on which a subject having a pigmented lesion is placed; and
    a photo detector for receiving an interference signal produced by superposition of the first split beam reflected from the reference stage and the second split beam reflected from first and second boundary layers of the pigmented lesion;

the reflected second split beam including a first boundary layer reflected split beam and a second boundary layer reflected split beam;

a beam path distance corresponding to the first split beam being $L_1$, a beam path distance corresponding to the first boundary layer reflected split beam being $L_2$, and a beam path distance corresponding to the second boundary layer reflected split beam being $L_2+d$, d being a distance difference between the first boundary layer and the second boundary layer; and a first path difference being $L_1-L_2$ and a second path difference being $L_1-(L_2+d)$;

wherein the interference signal corresponds to the first path difference and the second path difference;

the system further comprising a controller for calculating size information of the pigmented lesion using phase information of the interference signal;

wherein the sample stage is configured to two-dimensionally scan the second split beam to obtain three dimensional (3D) phase information of a phase of the interference signal;

wherein the calculating size information comprises calculating an amount of change in the phase by computing a change in mean free path according to scattering characteristics per particle size from a three dimensionally phase-mapped image corresponding to phase data measured for the interference signal; and the controller is configured to control the reference mirror to adjust $L_{offset}$, wherein $L_{offset}=L_1-L_2$, by changing a path length of the first split beam so that $L_{offset}$ is within a predetermined range.

5. The system of claim 4, wherein the controller is configured to:

map the phase of the interference signal onto an image and calculate the amount of change of the phase from the image, and calculate size information of the pigmented lesion from the amount of change of the phase.

* * * * *